United States Patent [19]

Anno et al.

[11] Patent Number: 4,606,631
[45] Date of Patent: Aug. 19, 1986

[54] PARTICLE COUNTER

[75] Inventors: Gousuke Anno; Yoshinori Suzuki, both of Yokohama, Japan

[73] Assignee: Kabushiki Kaisha Toshiba, Kawasaki, Japan

[21] Appl. No.: 607,311

[22] Filed: May 4, 1984

[30] Foreign Application Priority Data

May 12, 1983 [JP] Japan .................................. 58-83422
May 12, 1983 [JP] Japan .................................. 58-83423

[51] Int. Cl.$^4$ ........................ G01N 33/49; G01N 1/14
[52] U.S. Cl. .................................... 356/39; 250/574; 356/338; 422/67
[58] Field of Search .............................. 356/335–338, 356/39, 70, 72–73, 317, 318, 246, 440; 250/573–576, 459.1, 461.2; 377/10–12; 324/71.4, 71.1; 422/67

[56] References Cited

U.S. PATENT DOCUMENTS

| 3,661,460 | 5/1972 | Elking et al. | 356/335 X |
| 3,790,760 | 2/1974 | Stiller | 356/335 X |
| 3,845,309 | 10/1974 | Helm et al. | 356/317 X |
| 4,129,381 | 12/1978 | Wied et al. | 356/73 X |
| 4,178,103 | 12/1979 | Wallace | 356/246 X |
| 4,367,043 | 1/1983 | Sweet et al. | 356/338 |
| 4,428,669 | 1/1984 | Bessis | 356/39 |
| 4,510,438 | 4/1985 | Aver | 356/335 X |
| 4,522,493 | 6/1985 | Tamagawa et al. | 356/39 X |

FOREIGN PATENT DOCUMENTS 0107333 2/1984 European Pat. Off. .
7500390 7/1976 Netherlands .

OTHER PUBLICATIONS

The Review of Scientific Instruments; vol. 43, No. 3, Mar. 1972, pp. 404–409, "Fluorescence Activated Cell Sorting", L. A. Herzenberg et al.

Primary Examiner—Vincent P. McGraw
Assistant Examiner—Robert Thompson, III
Attorney, Agent, or Firm—Oblon, Fisher, Spivak, McClelland & Maier

[57] ABSTRACT

A first syringe pump feeds a sample solution such as, for example, a diluted blood into an inner tube of a flow cell, and a second syringe pump feeds a sheath solution such as, for example, a physiological saline solution into an outer tube of the flow cell. Respective first and second plungers of the first and second syringe pumps are fixed onto a connecting plate. The connecting plate is supported by a pair of guide rods so that it may be moved in line with the moving direction of the plungers. Into the connecting plate is screwed an externally threaded rod, which is driven by a motor to rotate in the normal and reverse directions about its axis. By the normal and reverse rotations of the threaded rod, the connecting plate is reciprocally moved, whereby the first and second plungers are moved at the same speed. By the movement of the first and second plungers at the same speed, the sample solution and the sheath solution are respectively fed into the flow cell at the same rate. Thus, in the flow cell, two flows of solution (water sheath), consisting respectively of the sample solution and the sheath solution existing around the sample solution, are formed. Laser beams are irradiated onto the flow of sample solution of the water sheath passing through a small-diameter portion of the flow cell, whereby the laser beams scattered by grains (blood corpuscles) in the sample solution are sensed by a beam sensor.

9 Claims, 5 Drawing Figures

PARTICLE COUNTER

BACKGROUND OF THE INVENTION

The present invention relates to a particle counter (hereinafter referred to as a "grain" counter) such as, for example, a blood corpuscle counter for measuring the size of a blood corpuscle and the number of blood corpuscles, thereby examining the blood and, more particularly, to a grain counter which makes it possible to obtain a fine, stable blood column.

In a blood corpuscle counter, in order to increase the measuring precision, it is necessary to cause diluted blood to flow into a pipe having a small inner diameter and make the region to be measured by a sensor small. However, blood to be measured sometimes contains dust, which is introduced when it is extracted, or coagulated components. When such blood is allowed to flow through the fine pipe, the interior of the pipe is blocked. This is one of the drawbacks inherent in this type of blood corpuscle counter.

A water sheath technique has been proposed for eliminating this drawback. In FIG. 1, a type view showing the water sheath principle is shown. A flow cell 10 has an outer tube 12 and an inner tube 14, for example, concentrically disposed in the outer tube 12. A sample solution 18 such as, for example, diluted blood is allowed to flow through the inner tube 14 in a direction indicated by a solid line. On the other hand, a sheath solution 16 such as, for example, physiological saline solution is allowed to flow through the interspace between the outer tube 12 and the inner tube 14 in a direction indicated by a broken line. At a terminal end of the inner tube 14, two flows of solution, consisting respectively of a solution column of sample solution 18 and the sheath solution enclosing this solution column, are created. By reducing the inner diameter of the outer tube 12 having no inner tube 14 disposed therein, the diameter of the two-flow unit consisting of the sheath solution 16 and the sample solution 18 is reduced, whereby a water sheath is formed wherein a fine flow of sample solution 18 is sheathed by the sheath solution 16. In this case, the inner diameter of the inner tube 14 through which the sample solution is allowed to flow can be made large enough to prevent the interior of the inner tube from being blocked by the sample solution 18. On the other hand, even when the cross sectional column of sample solution is reduced by the small-diameter portion 13 of the outer tube 12, this small-diameter portion can not be blocked by the sample solution 18 since the sheath solution 16 exists around the column of sample solution.

By the way, in a conventional blood corpuscle the water sheath is formed with the use of the device shown in FIG. 2. The outer tube 12 is connected to a closed talk or reservoir 20 by means of a pipe 22. On the other hand, the inner tube 14 is connected to a closed reservoir 24 by means of a pipe 26, The reservoirs 20 and 24 are connected to a compressed air supply source by means of pipes 28 and 30, respectively so that compressed air may be supplied to the reservoirs 20 and 24, respectively. By supplying two sources of compressed air with pressures of P1 and P2 to the closed reservoirs 20 and 24, respectively, the sheath solution 16 and sample solution 18 are supplied to the outer tube 12 and the inner tube 14 through the pipes 22 and 26, respectively.

In this type of device, however, it is necessary to precisely adjust the difference between the pressures P1 and P2 of the compressed air, used to deliver the sheath solution 16 and the sample solution 18, to a specified value. Further, where water impurities, proteins in the blood, or the like are adhered onto the inner wall surface of the pipes 22 and 26, whereby the flow resistance in the pipes 22 and 26 varies, the column of sample solution of the water sheath is varied in diameter, or in the worst case the water sheath is not formed. This constitutes one of the drawbacks inherent in the conventional device.

SUMMARY OF THE INVENTION

The object of the present invention is to provide a simply constructed grain counter which is capable of reducing the cross sectional column of sample solution of the water sheath to a stable and constant diameter and thereby measure the size and number of grains with high precision.

According to the present invention, there is provided a grain counter so arranged as to form a water sheath consisting of two flows of solution, consisting respectively of a flow of sample solution and a flow of sheath solution existing around the flow of sample solution, thereby sensing the state of the grains contained in the flow of sample solution.

This grain counter comprises: a sample solution receptacle for storing a sample solution therein; a sheath solution receptacle for storing a sheath solution therein, a flow cell having an inner tube connected to the sample solution receptacle and an outer tube connected to the sheath solution receptacle, whereby to form a flow of sheath solution, supplied to the outer tube, around a flow of sample solution, supplied to the inner tube, thereby to form a water sheath consisting of such two flows of solution; and a measuring means for sensing the state of the grains contained in the flow of sample solution.

A first syringe pump has a first plunger, the movement of which causes the sample solution to be sucked from the sample solution receptacle and this sample solution to be supplied into the inner tube of the flow cell.

A second syringe pump has a second plunger, the movement of which causes the sheath solution to be sucked from the sheath solution receptacle and this sheath solution to be fed into the outer tube of the flow cell.

A connecting member connects the first plunger and second plunger, said connecting member being moved by a drive means, whereby the first and second plungers are moved at the same speed.

The present invention can provide a stable water sheath since the plungers supply sheath solution and sample solution directly to the flow cell at a constant speed. Since both plungers are mechanically connected, they are moved at the same speed and in the same direction. With a simple construction, therefore, the cross sectional flow of sample solution of the water sheath can be reduced to a specified and stable diameter without using a complicated controlling means. For this reason, the grain counter according to the present invention makes it possible to measure the state of grains such as the size, number, etc. thereof with high precision.

Further, according to the present invention, since the state of grains is measured by utilizing a water sheath, the flow of sample solution can not be blocked during the process of its measurement. Further, since the grains flow or pass through a specified position of the flow cell, no variation in sensitivity occurs during the sensing step, due to the variation in position of passing of the grains, whereby it is possible to make measurement of the grain with high precision. Further, according to the present invention, since the diameter of the flow of sample solution can be reduced to prevent two or more grains (blood corpuscle) from existing in the area of measurement, it is possible to precisely measure the number of the grains.

DETAILED DESCRIPTION OF THE PREFERRED EMBODIMENTS

Figure 1:
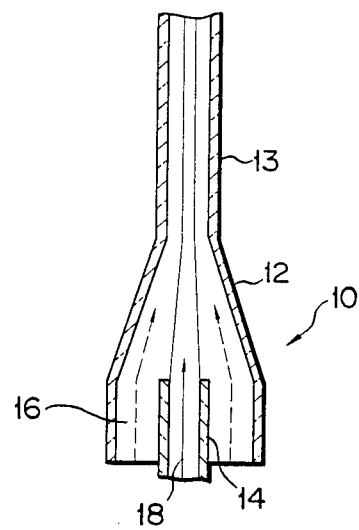
FIG. 1 is a type view showing the principle of a water sheath.
Figure 2:
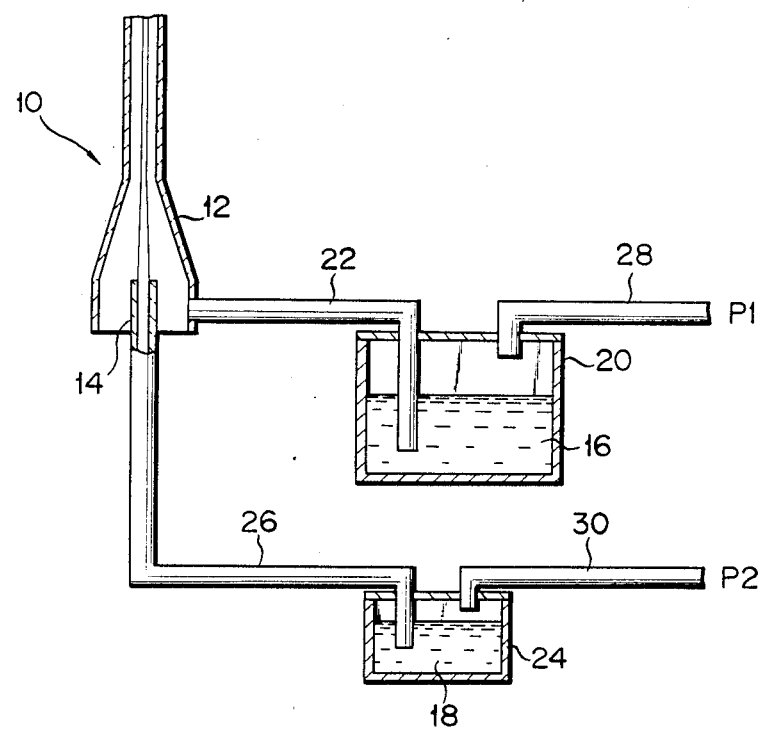
FIG. 2 is a type view showing a prior art grain counter.
Figure 3:
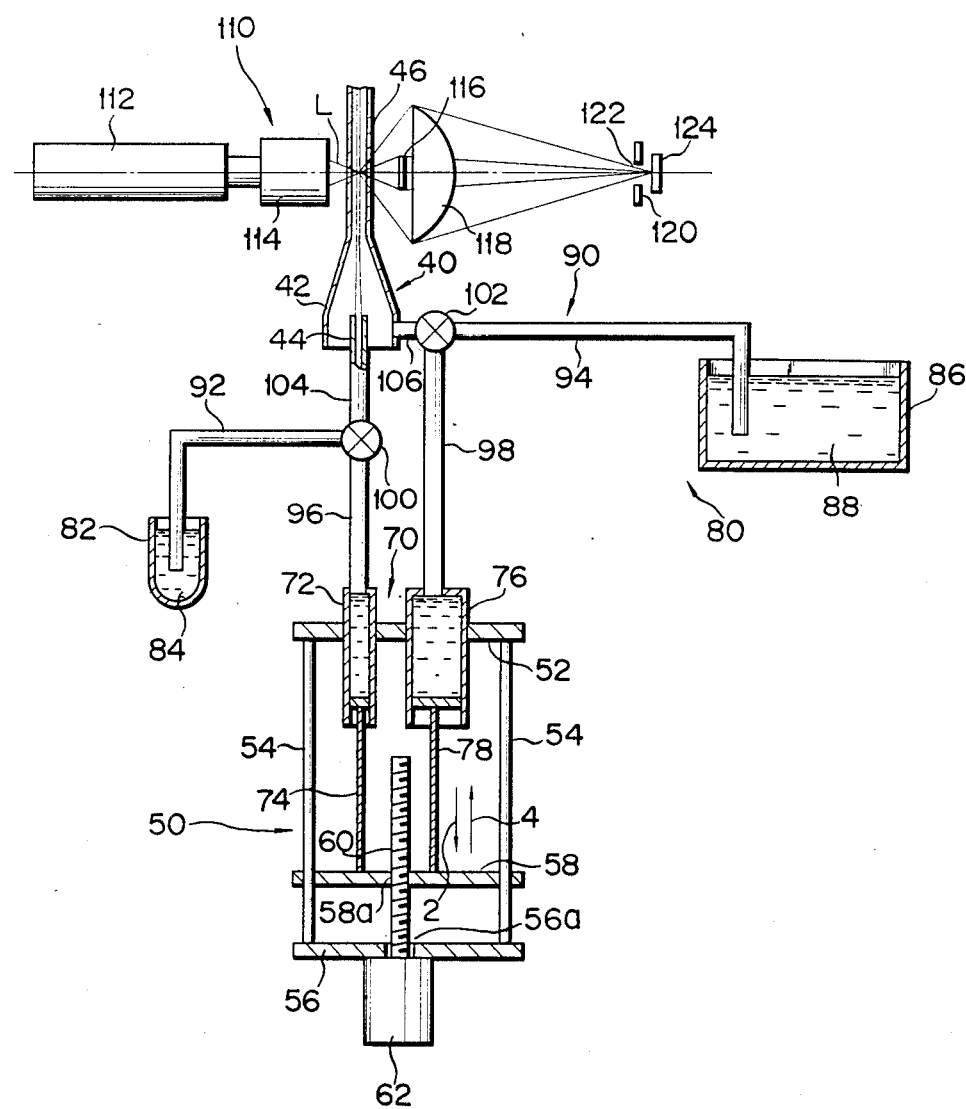
FIG. 3 is a type view of a grain counter according to an embodiment of the present invention.

In FIG. 3, a blood corpuscle counter as a grain counter, according to a first embodiment of the invention, is shown. A flow cell 40 is made of a material such as glass which is capable of transmitting a light therethrough. It is constructed in the same manner as that in which a flow cell 10 (see FIG. 1) is constructed, and has an outer tube 42 and an inner tube 44. Within a first receptacle 82 is stored a sample solution 84, i.e., diluted blood. Within a second receptacle 86 is stored a sheath solution 88, that is, a dilute solution such as, for example, physiological saline solution. The receptacle 82 is connected to the inner tube 44 of the flow cell 40 through a pipe 92 and a pipe 104 while, on the other hand, the receptacle 86 is connected to the outer tube 42 of the flow cell 40 through a pipe 94 and a pipe 106. Tip ends of the pipes 92 and 94 are immersed in the sample solution 84 and the sheath solution 88 in the receptacles 82 and 86, respectively. Three-way valves 100 and 102 are disposed between the pipes 92 and 104 and between the pipes 94 and 106, respectively.

Syringe pumps 72 and 76 are connected to the three-way valves 100 and 102, respectively, through a pipe 96 and a pipe 98. Each pipe 92, 94, 96, 98, 104 or 106 is for example 2 mm in inner diameter. The pipes 96 and 98 in particular are respectively long enough to store therein a sample solution for the examination of blood and a sheath solution. The syringe pumps 72 and 76 are, for example, 1 mm and 10 mm in inner diameter, respectively. The volume (inner cross sectional area) of the syringe pump 76 is approximately one hundred times as great as that of the syringe pump 72. The syringe pumps 72 and 76 are fixed to a support plate 52 in a manner that their longitudinal directions are allowed to intersect the support plate 52 at right angles thereto. A pair of guide rods 54 are fixed to the support plate 52 in such a manner that they intersect the support plate 52 at right angles thereto. A fixing plate 56 is fixed to the guide rods 54 in a manner that it is parallel to the support plate 52. Respective tip ends of the plungers 74 and 78 of the syringe pumps 72 and 76 are mechanically fixed to a connecting plate 58, through which the guide rods 54 are inserted. Said connecting plate 58 is thus arranged to reciprocatingly move along the guide rods 54. By this reciprocating movement of the connecting plate 58, the plungers 74 and 78 can be reciprocally moved through the cylinders of the syringe pumps 72 and 76 at the same speed and in interlocking relation with each other, respectively. On the outer surface of the fixing plate 56, a reversible motor 62 is provided in such a manner that its rotation shaft is extended through an insertion bore 56a provided in the fixing plate 56 and protruded therefrom toward the support plate 52. On the rotation shaft of the reversible motor 62, a screw rod 60 is fixed with its axis being in alignment with that rotation shaft, said screw rod being formed with an external thread on its outer peripheral surface. The screw rod 60 is screwed into a threaded bore 58a formed in the connecting plate 58. Thus, by the rotation of the screw rod 60, the connecting plate 58 can be reciprocally moved along the guide rods 54.

In the flow cell 40, a portion of the outer tube in which the inner tube 44 does not exist is reduced in its outer diameter, thus constituting a small-diameter portion 46. On this small-diameter portion 46, a measuring means 110 for examining a blood is disposed. The measuring means 110 comprises two sections disposed on both sides of the small-diameter portion 46 which serves as a center; one section is a laser beam irradiation section and the other is an optical sensor section. The laser beam irradiation section has a laser beam emission means 112 and an optical lens means 114 for focussing the laser beams emitted from the laser beam emission means 112. The laser beams, after they are reduced in amount, are irradiated into the liquid or solution in the small-diameter portion 46. On the other hand, the optical sensor section has a beam stopper 116 disposed so as to be in coincidence with the axes of the laser beams irradiated onto a small-diameter portion 46, a condenser 118, a slit 120 and an optical sensor 124. Of the laser beams irradiated onto the small-diameter portion 46, those which have passed straight through the small-diameter portion 46 are intercepted by the beam stopper 116. On the other hand, those which have been scattered at the small-diameter portion 46 and have not been intercepted by the beam stopper 116 are condensed by the condenser 118. The laser beams thus condensed pass through a pin hole 122 of the slit 120 and then are sensed by the optical sensor 124.

The operation of the blood corpuscle counter having the above-mentioned construction will now be described. First, the cross valves 100 and 102 are respectively set so as to permit the pipes 92 and 94 to communicate with the pipes 96 and 98, respectively. Thereafter, the reversible motor 62 is driven to rotate whereby the screw rod 60 is rotated, whereby the connecting plate 58 is moved in a direction indicated by an arrow 2. As a result, the plungers 74 and 78 are moved in a direction to be withdrawm from the syringe pumps 72 and 76, respectively. As a result, the sample liquid 84 and sheath solution 88 in the receptacles 82 and 86 are sucked by the syringe pumps 72 and 76, respectively. After specified amounts of sample solution 84 and sheath solution 88 have been sucked by the syringe pumps 72 and 76 and received in the pipes 96 and 98 respectively, the rotation of the motor 62 is stopped. Subsequently, the three-way valves 100 and 102 are so switched as to permit the communication of the pipe 96 with the pipe 104 and the communication of the pipe 98 with the pipe 106. Thereafter, the motor 62 is driven in reverse rotation causing the screw rod 60 to rotate in sheath solution 88 in the receptacles 132 and 86 are sucked into the syringe pumps 72 and 76, respectively. After a specified amount (which corresponds to a pipe length of, for example, two or three centimeters) of the sample solution is sucked into the pipes 96a and 130, the rotation of the reversible motor 62 is stopped. Subsequently, the tip end of the pipe 130 is immersed into the cleaning liquid solution 138 in the receptacle 136 by the switching means 128. Subsequently, the three-way valve 140 is so switched as to connect the pipe 96a and the pipe 142, and then the plunger 146 is moved in the direction indicated by the arrow 6. The movement of this plunger can be made by rotation of a motor, as in the case of the plungers 74 and 78. By the movement of the plunger 146 in the direction indicated by the arrow 6, the cleaning liquid solution 138 in the receptacle 136 is sucked into the pipe 130. When the cleaning liquid in the pipe 130 has passed through the three-way valve 100 and entered the pipe portion 96a, the movement of the plunger 146 is stopped. Subsequently, the three-way valve 100 is so switched as to connect the pipe 104 and the pipe portion 96a. Subsequently, a motor, used to drive the plunger 146, is rotated in the reverse direction, thereby to move the plunger 146 in the direction indicated by the arrow 8. Thus, the cleaning liquid and the sample solution in the pipes 96a and 142 flow through the pipe 104 and are thus supplied into the flow cell 40. At this time, the sample solution and cleaning solution are not mixed together and flow toward the flow cell 40 in a state wherein the sample solution immediately follows the cleaning liquid. Accordingly, since the interiors of the pipe 104 and inner tube 44 are washed by the forward cleaning liquid, it is impossible that the sample solution is contaminated by a sample solution used in the preceding examination. At the time when the sample solution has arrived at a position immediately before the flow cell 40, the plunger 146 is stopped from being moved. Subsequently, the three-way valve 140 is switched so as to allow the communication of the pipe portion 96a with the pipe portion 96b, while on the other hand, the three-way valve 102 is switched so as to allow the communication of the pipe 98 with the pipe 106. The reversible motor 62 is rotated, causing the screw rod 60 to rotate about its axis and the connecting plate 58a moves in the direction indicated by the arrow 4. Thus, as in the preceding embodiment shown in FIG. 3, the sample solution 134 is fed into the inner tube 44 of the flow cell 40, and the sheath solution 88 is fed into the outer tube 42. In the flow cell 40, a water sheath is formed with respect to the sample solution. Thus, the size and the number of blood corpuscles in the flow of the diluted blood, as water-sheathed, are measured by the measuring means 110 in the same procedure as in the preceding embodiment of FIG. 3.

Figure 4:
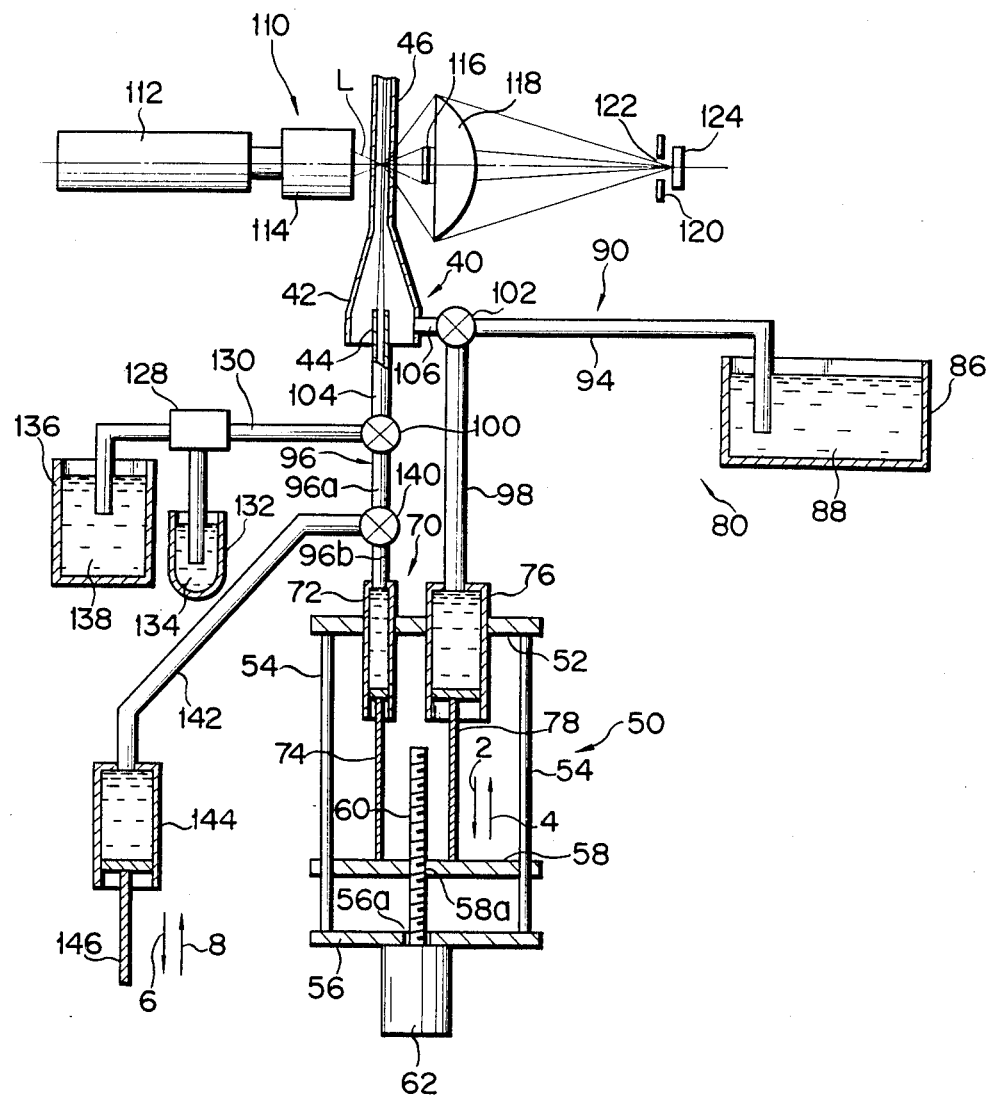
FIG. 4 is a type view of the grain counter according to another embodiment of the present invention; and, FIG. 5 is a type view showing a part of the grain counter according to still another embodiment of the present invention.

In this second embodiment, the same effects as those obtained in the preceding first embodiment of FIG. 3 are obtained. At the same time, the second embodiment also has the effect of avoiding the useless consumption of a sample solution, or blood. That is to say, in the embodiment of FIG. 3, of the sample solution sucked into the pipes 92 and 96, the part left in the pipe 92 when the three-way valve 100 is switched to allow the communication between the pipes 96 and 104 is thrown away. In the embodiment of FIG. 4, however, the sample solution sucked out of the receptacle 132 is wholly fed into the flow cell 40 and used for measurement of the blood corpuscles contained therein.

Moreover, in the embodiment as well shown in FIG. 3, it is possible to avoid the useless consumption of the sample solution by installing a receptacle having a cleaning liquid therein in addition to the receptacle 82 having the sample solution 84 therein and moving the pipe 92 from one of these receptacles to the other. In this case, however, since the sucking and discharging of the sample solution and cleaning liquid solution are performed with the use of the single syringe pump 72, the following drawbacks are produced.

That is to say, it is necessary to suck a volume cleaning liquid large enough to fill the pipe 92. On the other hand, although it is sufficient to suck only a small amount of sample solution, it is necessary to make the rate of feeding such sample solution to the flow cell 40 constant. When, in this case, an attempt is made to reduce the syringe diameter and thereby increase the degree of permission of error taken with respect to the distance of movement of the plunger, at the time of sucking and discharging the cleaning liquid the plunger must be moved over a great length. This means that a large amount of time is required for sucking the cleaning liquid solution. On the other hand, when the syringe diameter is increased for the purpose of quickly feeding a large volume of cleaning liquid, at the time of feeding a small amount of sample solution it becomes difficult to keep a precise feeding rate of the sample solution at a constant value because of the short moving distance of the plunger 74. When the rate of feeding the sample solution is varied, the diameter of the flow of sample solution (the flow of diluted blood) is varied with the result that the precision with which the blood corpuscles are measured decreases.

In contrast, in the embodiment of FIG. 4, the sample solution 134 is sucked and discharged by the syringe pump 72, while the cleaning liquid 138 is sucked and discharged by the syringe pump 144 with a capacity larger than that of the syringe pump 72. Accordingly, where the sample solution is fed, it is possible to keep a precise feeding rate at a constant value because of the long moving distance of the plunger. And where the cleaning liquid is fed, it is possible to suck and discharge it at high rate. According to this second embodiment, therefore, it is possible to measure the blood corpuscles quickly with high precision.

Figure 5:
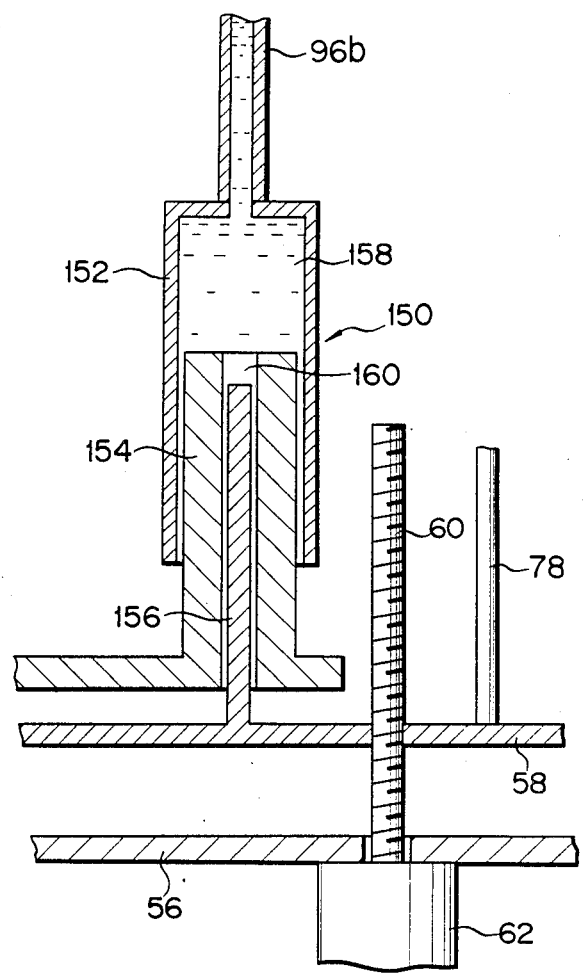

The blood corpuscle counter according to a third embodiment of the invention will now be described with reference to FIG. 5. In this third embodiment, the syringe pump 72 and the syringe pump 144 are made into an integral pump unit. The third embodiment is the same as the embodiment of FIG. 4, except that in FIG. 5 a syringe pump 150 is provided in place of the syringe pump 72 and that the three-way valve 140, pipe 142, syringe pump 144, and plunger 146 are not provided. The syringe pump 150 has a large-diameter cylinder 152 connected to the pipe portion 96b, a large-diameter piston 154, and a small-diameter piston 156. The piston 154 is inserted into a hollow portion 158 of the cylinder 152. The piston 154 is made substantially cylindrical, and the piston 156 is inserted into a hollow portion 160 of the piston 154. The piston 156 has its one end fixed on the connecting plate 58 and is moved interlockingly with the plunger 78. On the other hand, the piston 154 is connected to another moving means, whereby it can be moved separately from, or independently of, the piston 156.

In this third embodiment, the sample solution in the receptacle 132 is sucked by the movement of the piston the opposite direction which causes the connecting plate 58 to move in a direction indicated by an arrow 4. Thus, the plungers 74 and 78 are moved, in a state wherein they are interlocked, at the same speed (for example, 1.25 mm/sec) in the direction indicated by the arrow 4. The sample solution and sheath solution in the syringe pumps 72 and 76 are allowed to flow through the pipes 96 and 104 and the pipes 98 and 106, respectively, to be fed into the flow cell 40. In the flow cell 40, two flows of solution, consisting respectively of a solution column of sample solution and a sheath solution existing around the column of sample solution, are thus formed from the sample solution and sheath solution fed thereinto. This two-flow unit consisting of the sheath solution and the sample solution is reduced in cross section by the small-diameter portion 46 of the outer tube 42, whereby a water sheath is formed. The sample solution thus reaches, in the form of such a water sheath, the measuring means 110 after passing through the small-diameter portion 46.

In this case, the radius r of the sample solution reduced in cross section to form a water sheath can be expressed by the formula (1) below.

$$r = \sqrt{Sf \cdot Sb/\pi (Ss + Sb)} \tag{1}$$

where Sf represents the cross sectional area of the small-diameter portion 46 of the flow cell 40, Ss the cross sectional area of the plunger 78 for feeding the sheath solution (the cross sectional area of the interior of the syringe pump 76), and Sb the cross sectional area of the plunger 74 for feeding the sample solution (the cross sectional area of the interior of the syringe pump 72). Since the cross sectional area of the interior of the syringe pump 76 is much greater than that of the syringe pump 72 ($Ss >> Sb$), the following formula (2) holds true.

$$r = \sqrt{Sf \cdot Sb/\pi \cdot Ss} \tag{2}$$

Ss should be much greater than Sb. If Ss and Sb were similar, r would be determined by Sf as evident from equation (1). To reduce r, Sf must be small. In practice, it is difficult to reduce Sf. As understood from equation (2), r does not depend on the velocity of the solution. It is determined by Sf, Sb and Ss. In other words, r is constant regardless of the changes in operation conditions.

For example, when it is assumed that the inner diameter of the syringe pump 76 is 10 mm; the inner diameter of the syringe pump 72 is 1 mm; and the inner diameter of the small diameter portion 46 is 0.2 mm, then the flow of the sample solution existing at the small-diameter portion 46 becomes approximately 22 $\mu$m in diameter. This means that the flow of sample solution has a reduced diameter which permits one blood corpuscle to flow through.

The laser beams emitted from the laser beam emission means 112 are irradiated onto the flow of sample solution in the small-diameter portion 46 after being focussed or condensed by the optical lens means 114. Where no blood corpuscle exists in the irradiated spot of the flow of sample solution, the laser beams pass straight through such an irradiated spot and are intercepted by the beam stopper 116. Accordingly, it is impossible that those laser beams are sensed by the optical sensor means or beam sensor 124. On the other hand, where any blood corpuscle exists in said irradiated spot, part of the laser beams is scattered by that blood corpuscle. Of the laser beams thus scattered, a part not intercepted by the beam stopper 116 is condensed by the lens 118. Of these laser beams, a part having passed through the slit 120 is sensed by the beam sensor 124.

A specified relation exists between the intensity of the laser beam sensed by the beam sensor and the size of a blood corpuscle. This specified relation is such that as the size of a blood corpuscle increases, the intensity of the scattered beams increases. By using this specified relation, it is possible to know the size of a blood corpuscle from the intensity of the scattered beams. In the case of a sample solution prepared by diluting blood to a concentration several hundreds of times lower than the original concentration of the blood, it is possible that no blood corpuscle at all exists in the flow of such a sample solution allowed to flow through the laser-beam irradiated spot or area of the small-diameter portion 46. Thus, by determining the frequency at which the intensity of the scattered beam sensed by the beam sensor increases, it is possible to know the number of blood corpuscles involved.

The blood corpuscle counter according to a second embodiment of the invention will now be described with reference to FIG. 4. This second embodiment is so arranged as to prevent blood from being left in the pipes, so as to effectively utilize the blood. In FIG. 4, the same members and portions or sections as those shown in FIG. 3 are denoted by the same reference numerals and their descriptions are omitted.

In this embodiment, a pipe 130 in place of the pipe 92 is connected to the three-way valve 100. The pipe 130 is introduced into the sample solution 134 stored in a receptacle 132. On the other hand, a cleaning liquid 138 such as, for example, a physiological saline solution, which is similar to the sheath solution 88, is received in a receptacle 136. A tip end portion of the pipe 130 can also be immersed into the cleaning liquid 138 in the receptacle 136. According to this second embodiment, a switching means 128 selectively switches the pipe 130 to one of the receptacles 132, 136 from the other for effecting the communication between both.

A three-way valve 140 is mounted between a pipe portion 96a and a pipe portion 96b of the pipe 96. To the three-way valve 140 is connected a pipe 142, to which is connected a large capacity syringe pump 144 having an inner diameter of, for example, 10 mm. A plunger 146 of the syringe pump 144 can be reciprocally moved in directions 6 and 8 to permit the matter in the syringe pump 144 to be either discharged from or sucked into the syringe pump.

The operation of the blood corpuscle counter having the above-mentioned construction will now be described. The three-way valves 100, 102 and 104 are mounted at positions connecting the pipes 96 and 130, the pipes 94 and 98, and the pipe portions 96a and 96b, respectively. The pipe 130 is immersed in the sample solution 134 received or stored in the receptacle 132. In this state, the reversible motor 62 is driven to rotate. Thus, the connecting plate 58 is moved in the direction indicated by the arrow 2 by the resultant rotation of the screw rod or externally threaded rod 60 kept in screw engagement with the threaded bore 58a. Thus, the plungers 74 and 78 are moved in the direction in which they are withdrawn from the syringe pumps 72 and 76, respectively. Thus, the sample solution 134 and the 156, resulting from the movement of the connecting plate 58, while the cleaning liquid solution 138 in the receptacle 136 is sucked by moving the piston 154 via another moving means. In this third embodiment as well, the blood corpuscles can be examined quickly with high precision as in the case of the preceding embodiment shown in FIG. 4.

In the above-mentioned embodiments, the state of grains (blood corpuscles) is measured with the use of laser beams. In this case, since the magnitude or largeness of a detection signal can be increased by reducing the laser beam in its cross sectional area, the S/N ratio can be made great. In the present invention, however, the state of grains can be also measured, not by detection of the scattered beams as above, but through the use of other suitable measuring means such as, for example, detection of transmission lights, detection of electric resistance, detection of electrostatic capacity, etc. Further, the present invention may also be constructed in various forms of counters other than the blood corpuscle counter, e.g., those for measuring grains such as impurities contained in an oil, dusts contained in a pure water, or the like. Further, the device means for the connecting members may be other suitable drive means than the screw rod and motor used in the above-mentioned embodiments, such as, for example, a drive means based on the use of worm gears or cam mechanism.

What is claimed is:

1. A grain counter for forming a water sheath consisting of two flows of solution one of which is a flow of sample solution and the other of which is a flow of sheath solution existing around the flow of sample solution and sensing the state of the grains contained in the flow of sample solution, comprising:
    a sample solution receptacle for storing therein a sample solution,
    a sheath solution receptacle for storing therein a sheath solution,
    a flow cell having an inner tube connected to said sample solution receptacle and an outer tube connected to said sheath solution receptacle and forming a flow of said sheath solution fed into said outer tube around a flow of said sample solution fed into said inner tube thereby producing a water sheath consisting of said two flows of solution,
    a measuring means for sensing the state of the grains contained in said flow of sample solution of said water sheath,
    a first syringe pump having a first plunger and sucking said sample solution from said sample solution receptacle by the movement of said first plunger and feeding said sample solution into said inner tube of said flow cell,
    a second syringe pump having a cross sectional area greater than that of said first syringe pump, said second syringe pump having a second plunger and sucking said sheath solution from said sheath solution receptacle by the movement of said second plunger and feeding said sheath solution into said outer tube of said flow cell,
    a connecting member to which said first and second plungers are mechanically connected,
    a drive means for moving said connecting member, thereby moving said first and second plungers at the same speed,
    a first three-way valve,
    a second three-way valve,
    first, second, and third pipes connecting said first three-way valve to the sample solution receptacle, said first syringe pump, and said inner tube, respectively, and
    fourth, fifth, and sixth pipes connecting said second three-way valve to the sheath solution receptacle, said second syringe pump, and said outer tube, respectively,
    whereby, when said first or second syringe pump sucks said sample solution or sheath solution in said sample solution receptacle or sheath solution receptacle, respectively, said first or second three-way valve is set so as to allow the communication between said first and second pipes, or the communication between said fourth and fifth pipes, and whereby, when said first and second syringe pump feeds said sample solution or sheath solution, respectively, into said inner tube or outer tube, said first and second three-way valves are respectively set so as to allow the communication between said second and third pipes, or the communication between said fifth and sixth pipes.

2. A grain counter according to claim 1, which further comprises a guide means for guiding said connecting member so as to permit its reciprocating movement in the directions in which said plunger is moved, a threaded bore provided in said connecting member, a screw rod screwed into said threaded bore, and a motor for rotating said screw rod, whereby said connecting member screwed onto said screw rod is reciprocally moved through the rotation of said screw rod by the rotation of said motor.

3. A grain counter according to claim 2, wherein said flow cell has a small-diameter portion which reduces the diameter of said water sheath consisting of said two flows of solution one of which is said flow of sample solution and the other of which is said flow of sheath solution; and said measuring means has a laser beam emission means for emitting laser beams, an optical lens means for focussing the laser beams emitted from said laser beam emission means so as to irradiate the laser beams onto said two flows of solution flowing through said small-diameter portion of said flow cell, and a beam sensor for sensing the laser beams scattered by the grains contained in said sample solution in said two flows of solution.

4. A grain counter according to claim 3, wherein said measuring means has a beam stopper disposed in alignment with an optical axis of said optical lens means so as to intercept the laser beams having passed straight through said samall-diameter portion, and a condenser for condensing the laser beams not intercepted by said beam stopper; and said beam sensor senses the laser beams condensed by said condenser.

5. A grain counter according to claim 1, which further comprises a cleaning liquid receptacle having a cleaning liquid stored therein, a switching means for selectively switching said first pipe to one of said sample solution and cleaning liquid receptacles from the other for effecting the communication between both, a third three-way valve mounted on a portion of said second pipe, a seventh pipe connected to said third three-way valve, a third syringe pump connected to said seventh pipe, said third syringe pump having a third plunger and having an inner cross sectional area greater than that of said first syringe pump, and a second drive means for reciprocally moving said third plunger, whereby, after said first syringe pump sucks said sample solution, said switching means switches said first pipe to permit the same to communicate with said cleaning liquid receptacle; said third three-way valve permits the communication of said second pipe with said seventh pipe; and thus said third syringe pump sucks said cleaning liquid.

6. A grain counter according to claim 5, wherein said third syringe pump sucks said cleaning liquid until no said sample solution is left in said first pipe; subsequently said first three-way valve is set so as to effect the communication of said second pipe with said third pipe; said third plunger is pushed into said third syringe pump to feed said sample solution up to a position immediately before said flow cell; subsequently said third three-way valve is set so as to effect the communication of said first syringe pump with said third pipe; and thus said first syringe pump feeds said sample solution into said flow cell.

7. A grain counter according to claim 5, wherein said third syringe pump has a cylinder; said third plunger has a cylindrical large-diameter piston; said first plunger has a small-diameter piston inserted into said large-diameter piston; and said first syringe pump is constituted by said large-diameter piston and said small-diameter piston.

8. A grain counter according to claim 1, wherein said sample solution is a diluted blood; said grain is a blood corpuscle; and said sheath solution is a physiological saline solution.

9. A grain counter according to claim 8, wherein said cleaning liquid is a physiological saline solution.

* * * * *